United States Patent [19]
Sabo et al.

[11] Patent Number: 5,928,882
[45] Date of Patent: Jul. 27, 1999

[54] TREATMENT AND PREVENTION OF NEURODEGENERATIVE DISEASES USING MODULATORS OF FE65

[75] Inventors: Shasta Sabo; Joseph D. Buxbaum; Paul Greengard, all of New York, N.Y.

[73] Assignee: The Rockefeller University, New York, N.Y.

[21] Appl. No.: 08/957,660

[22] Filed: Oct. 24, 1997

Related U.S. Application Data

[51] Int. Cl.$^6$ .................................................. G01N 33/55
[52] U.S. Cl. ........................ 435/7.21; 435/7.92; 435/70.1; 435/325; 435/350; 436/518; 436/536
[58] Field of Search ................................ 435/4, 7.1, 7.21, 435/7.92, 7.93, 7.94, 7.95, 325, 365, 366, 440, 455, 465, 70.1, 350; 436/518, 501, 536

[56] References Cited

PUBLICATIONS

Bork et al. (1995) Cell 80:693–4.
Borg et al. (1996) Mol. Cell. Biol. 16:6229–41.
Buxbaum et al., 1993, Proc. Natl. Acad. Sci. USA, 90: 9195–8.
Caporaso et al., 1992, PNAS, 89:2252–6.
Duilio et al., 1991, Nucl.. Acid. Res., 19:5269–74.
Esch et al., 1990, *Science*, 248: 1122–4.
Fiore et al., 1995, J. Biol. Chem., 270: 30853–6.
Glenner and Wang, 1984, Biochem. Biophys. Res. Com., 120: 885–90.
Goldgaber et al., 1987, Science, 235: 877–80.
Haass et al., 1992, Nature, 357: 500–2.
Haass et al., 1994, Proc. Natl. Acad. Sci. USA, 91: 1564–8.
Hwang et al. (1991) Sience 253:71–4.
Kang et al., 1987, Nature, 325:733–6.
McLoughlin et al. (1996) FEBS Lett. 397:197–200.
Seubert et al., 1992, Nature, 359: 325–327.
Shoji et al., 1992, Science, 258: 126–9.
Weidmann et al.,1989, Cell , 57: 115–26.
Zambrano et al., 1997, J. Biol. Chem., 272: 6399–405.
Zhang et al. (1997) EMBO J. 16:6141–50.

*Primary Examiner*—Patricia A. Duffy
*Attorney, Agent, or Firm*—Klauber & Jackson

[57] ABSTRACT

Modulators of the protein Fe65 can be utilized to affect the interaction of the protein Fe65 with the cytoplasmic domain of amyloid precursor protein and thus provide therapeutics for the treatment and/or prevention of neurodegenerative diseases, such as Alzheimer's disease and dementia.

4 Claims, 2 Drawing Sheets

TREATMENT AND PREVENTION OF NEURODEGENERATIVE DISEASES USING MODULATORS OF FE65

GOVERNMENT RIGHTS CLAUSE

This invention was made with government support under Grant No. NIH AG09464 awarded by the National Institutes of Health. The government has certain rights in the invention.

BACKGROUND OF THE INVENTION

Amyloid plaques are a major pathological hallmark of Alzheimer's disease. The principle component of amyloid plaques, Aβ,[1] is derived by proteolytic processing of the Alzheimer amyloid protein precursor (APP)[2,3]. APP is a Type I integral membrane protein expressed as three major alternatively spliced isoforms of 695, 751 and 770 amino acids in length. The 695 amino acid isoform is most abundant in neurons. APP is processed in two pathways by at least three unidentified proteases known as the α-, β- and γ-secretases.[4-6] Aβ is generated from cleavage by both β- and γ-secretase. α-secretase cleaves APP within the Aβ domain, precluding Aβ formation. The majority of processed APP is cleaved by α-secretase, releasing the large extracellular domain referred to as APPs. Both APPs and Aβ are secreted by normal cells.[4-8] However, the cells in Alzheimer patients abnormally allow the aggregation and accumulation of Aβ, and thus facilitate the formation of the amyloid plaques.

Fe65 is a brain-enriched protein of unknown function which binds to the NPTY sequence in the cytoplasmic tail of APP.[9-11] Fe65 contains two types of protein-protein interaction domains, the WW domain and the PI domain, binding APP through the second of its two PI domains.

SUMMARY OF THE INVENTION

The present invention relates to the discovery that proteins which bind to the cytoplasmic domain of APP regulate secretion of APP fragments. By intervening in the direct protein-protein interaction of Fe65 with APP, APP processing and trafficking, the progression and/or onset of Alzheimer's disease can be inhibited or prevented.

In accordance with the above, an assay system for screening potential drugs effective to modulate the interaction of the Fe65 with the APP can be prepared. The prospective drug is introduced into a system containing Fe65 and APP and the system thereafter examined to observe any changes in the interaction between the Fe65 and the APP due to the presence of the drug.

More particularly, this invention concerns a method for screening for agents capable of modulating the interaction of Fe65 and the cytoplasmic domain of amyloid precursor protein (APP) which comprises:

(a) providing a mammalian cell line which over-expresses both APP and Fe65 in culture;

(b) optionally, radioactively labeling proteins produced by said cells during anabolism; then (c) allowing the mammalian cells to continue metabolizing in a suitable label-free environment;

(d) contacting the mammalian cells at the start, or during step (c) with an agent suspected of being capable of modulating the interaction between Fe65 and the cytoplasmic domain of amyloid precursor protein;

(e) lysing the mammalian cells;

(f) measuring optionally labeled APPs and Aβ produced; and (g) comparing the measurements of step (f) with control cells not treated with the suspected agent.

Alternatively, agents may also be screened for their ability to interfere with the in vitro interaction of Fe65 with APP. Such in vitro studies can be performed with peptides corresponding to the binding domains of Fe65 and APP and/or with proteins derived from bacterial over-expression or from engineered cell lines. Effects on the interaction can be measured by surface plasmon resonance, energy transfer methods, coprecipitation, yeast interaction trap, and overlay blotting.

A further aspect of the present invention involves the method for preventing and/or treating neurodegenerative disease in a mammal in need of such therapy which comprises administration of a therapeutically effective amount of non-peptidyl agent capable of modulating the interaction of Fe65 and the cytoplasmic domain of amyloid precursor protein (APP).

It is thus an object of the present invention to provide a method of screening for agents useful for the prevention and/or treatment of neurodegenerative diseases, and especially Alzheimer's Disease.

It is also an object of the present invention to provide a mammalian cell line which over-expresses both APP and Fe65 in culture, so as to provide a facile and convenient method for identifying agents which modulate the interaction between Fe65 and APP.

It is a further object of the present invention to provide a screening assay for identifying agents which modulate the interaction between Fe65 and APP by utilizing peptides corresponding to the binding domains of Fe65 and APP and/or with proteins derived from bacteria over-expression or from engineered cell lines.

It is a still further object of the present invention to provide a method of preventing and/or treating neurodegenerative diseases, especially Alzheimer's disease by administration of a therapeutically effective amount of a non-peptidyl agent capable of modulating the interactive of Fe65 and the cytoplasmic domain, thereby reducing the amount of amyloid plaque in the central nervous system of the mammal under treatment.

Other objects and advantages will become apparent to those skilled in the art from a review of the ensuing description which proceeds with references to the following illustrative drawings.

BRIEF DESCRIPTION OF THE DRAWING FIGURES

FIG. 1 is a graph showing that over-expression of Fe65 causes an increase in secretion of APPs from MDCK cells. In these experiments, cells were pulsed with [$^{35}$S]-methionine for two hours, followed by a two-hour chase. APPs was immunoprecipitated from the chase medium with the monoclonal antibody, 6E10. Immunoprecipitated APPs was quantified by PhosphorImager. Values were normalized to total labeled cellular holoAPP immunoprecipitated, with the polyclonal antibody 369, from lysates collected before the chase. The data shown represents the mean ±SE pooled from three experiments (n=11).

FIG. 2A is a graph showing that over-expression of Fe65 causes an increase in Aβ secretion from MDCK cells. ELISA of conditioned medium from MDCK cells reveals an increase in Aβ secretion upon Fe65 expression. For these experiments, cells were incubated in serum-free medium for four hours at 37° C. Then, the medium was collected and subjected to a sandwich ELISA for Aβ using 4G8 as the capture antibody and FCA3340 or FCA3542 as the detection antibody. The values obtained are normalized to total cellular holoAPP determined by immunoblotting with 369. The results plotted represent the mean ±S.E. (n=12) for two experiments.

FIG. 2B is a gel showing the effect of Fe65 on Aβ secretion in the MDCK cells was confirmed by immunoprecipitation. These experiments were performed essentially as described above for APPs except Aβ was immunoprecipitated with both 6E10 and 4G8. The data shown are from a representative experiment.

DETAILED DESCRIPTION OF THE INVENTION

In accordance with the present invention there may be employed conventional prognostic, diagnostic, pharmaceutical and biological techniques within the skill of the art. Such techniques are explained fully in the literature.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduced by at least about 30 percent, more preferably by at least 50 percent, most preferably by at least 90 percent, the occurrence of amyloid formation.

The screening assays of the present invention are based on cell lines which over-express both APP and Fe65 and which can therefore be used to examine the effects of Fe65 on processing of APP. These cell lines are preferably Madin-Darby canine kidney (MDCK) cells stably expressing the 695 amino acid isoform of APP[12] (MDCK-APP) which were transfected with cDNA encoding Fe65 and selected for puromycin resistance. Doubly stable clonal cell lines (MDCK-APP/Fe65) were isolated using cloning rings, and cells expressing high levels of Fe65 were identified by immunoblotting with antibodies raised against the WW domain of Fe65.

Figure 1:
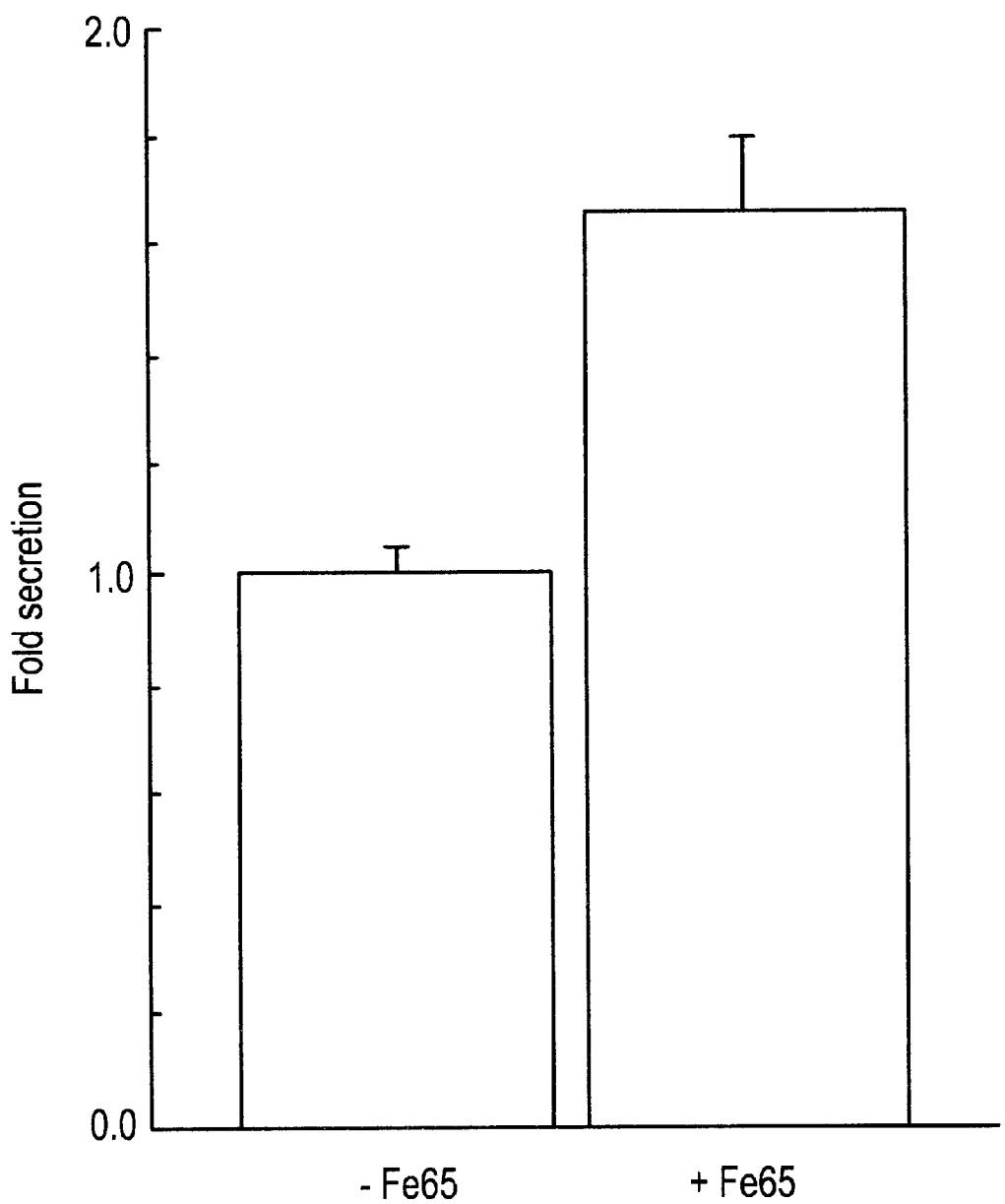

Immunoprecipitation of APPs from conditioned medium of [$^{35}$S]-methionine pulse-labeled MDCK-APP and MDCK-APP/Fe65 cells shows that over-expression of Fe65 increases secretion of APPs (FIG. 1). Secretion of APPs derived from newly synthesized APp is elevated by 67% (±14%) in an MDCK-APP/Fe65 cell line. Similar results were seen with another MDCK cell line over-expressing Fe65 when compared to transfection with empty vector alone. Interestingly, stable over-expression of Fe65 also caused enhanced APPs secretion from an MDCK cell line transiently transfected with APP-751 (data not shown). Thus, Fe65 causes an increase in APPs secretion from both neuronal and non-neuronal isoforms of APP.

Figure 2A:
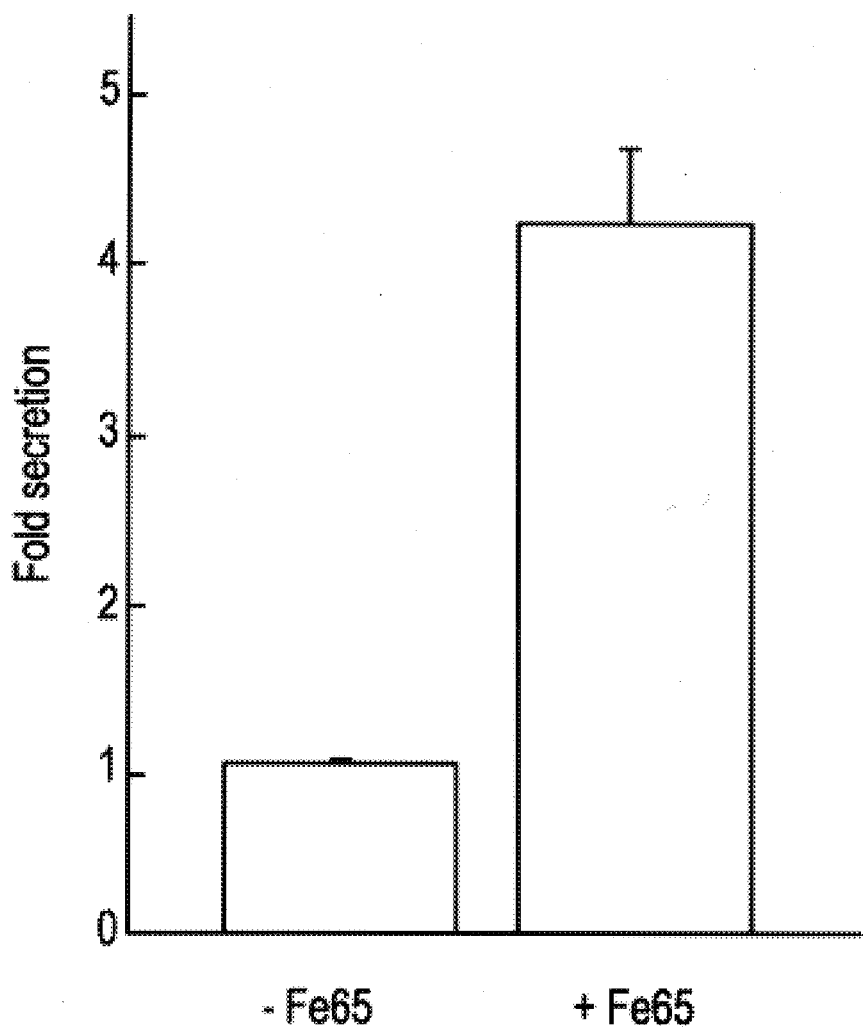
Figure 2B:
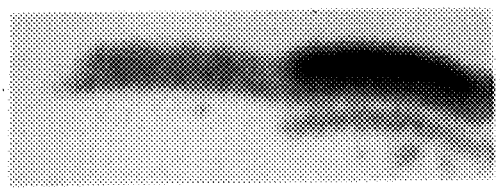

Since APPs release was increased, it was expected that Aβ secretion would be decreased. Surprisingly, Aβ secretion is increased approximately four-fold from MDCK-APP/Fe65 cells in both sandwich ELISA (FIG. 2A) and immunoprecipitation (FIG. 2B) experiments when compared to cells over-expressing APP alone. Similar results were seen in another MDCK cell line over-expressing Fe65 (data not shown).

α-cleavage of a molecule of APP prevents production of Aβ from the same molecule. Therefore, it is conventionally thought that large increases in secretion of APPs are accompanied by decreased Aβ formation. Using the cell lines of the present invention, the opposite effect is demonstrated, i.e., Fe65 over-expression yields enhanced APPs secretion concomitant with a dramatic increase in Aβ secretion. Whereas it was previously argued that therapies which increase APPs secretion should be effective in increasing Aβ secretion, the current findings imply that drugs that increase APPs secretion may not necessarily decrease Aβ secretion.

This is the first demonstration of an effect of a direct protein-protein interaction with APP on the proteolytic processing of APP. The results presented are contrary to conventional wisdom: the effects on Aβ and APPs are similar, whereas they were expected to be in opposite directions. Since the plasma membrane is a subcellular compartment at or near which both APPs and Aβ are thought to be produced, it is possible that Fe65 may either increase either the amount of APP transported from the Golgi to the plasma membrane or the amount of APP recycled back to the cell surface after endocytosis.

Alternatively, the peptides corresponding to the binding domains of Fe65 and APP, and/or with proteins derived from bacterial over-expression or from engineered cell lines can be utilized in a method for screening agents capable of modulating the interaction of Fe65 and APP, thereby preventing and/or mitigating the adverse effects of β-amyloid (AB) production.

The binding domain of Fe65 with APP has been described, for instance, in *J. Biol. Chem.* (USA), 1997, 272: 10, pp. 6399–6405. The two tandem phosphotyrosine interaction/phosphotyrosine binding (PID/PTB) domains of the Fe65 protein interact with the intracellular region of APP. Typically, the interaction can be measured, and the effect of the potential therapeutic agent under test, by a variety of methods such as surface plasmon resonance, energy transfer methods, coprecipitation, yeast interaction trap, or overlay blotting.

In one instance, the test drug can be administered to a cellular sample with Fe65 and APP, or the binding domains thereof, or an extract containing the Fe65 and APP, or the binding domains thereof, to determine its effect upon the activity of the binding of the Fe65 to the APP, by comparison with a control.

The assay system can be adapted to identify drugs or other entities that are capable of modulating the interaction of Fe65 with APP, by stimulating the production of APPs (soluble APP), thereby decreasing the amount of β-amyloid production. Such an assay would be useful in the development of drugs that would be specific against particular cellular activity, or that would potentiate such activity, in time or in level of activity.

The Fe65 and APP binding fragments can be used to produce antibodies to themselves and utilized as in tests for the presence of particular binding activity in suspect target cells. Antibody(ies) to the Fe65 and APP or their binding domain fragments can be produced and isolated by standard methods, including the well known hybridoma techniques.

The presence of Fe65 and APP in cells can be ascertained by the usual immunological procedures applicable to such determinations. A number of useful procedures are known. Especially useful procedures utilize either the Fe65 or APP, or their binding domain fragments, labeled with a detectable label, or their antibodies labeled with a detectable label.

The procedures and their application are all familiar to those skilled in the art and accordingly may be utilized within the scope of the present invention. The "competitive" procedure is described in U.S. Pat. Nos. 3,654,090 and 3,850,752. The "sandwich" procedure, is described in U.S.

Pat. Nos. RE 31,006 and 4,016,043. Still other procedures are known, such as the "double antibody," or "DASP" procedure.

In each instance, the Fe65 and APP form complexes with one or more antibody(ies) or binding partners and one member of the complex is labeled with a detectable label. The fact that a complex has formed and, if desired, the amount thereof, can be determined by known methods applicable to the detection of labels.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The Fe65 or APP, or their binding domain fragments, can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

An exemplary assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained, and the effects of the test drug can be compared to the results of the assay without the addition of the test drug.

Accordingly, a purified quantity of the Fe65 and the APP may be radiolabeled and combined, for example, with antibodies or other inhibitors thereto, after which binding studies, both with and without the test drug, can be carried out. Solutions are then be prepared that contain various quantities of labeled and unlabeled uncombined Fe65 and APP, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

In a further embodiment of the present invention, since Fe65 over-expression causes a profound increase in Aβ secretion, agents or drugs that inhibit the interaction of Fe65 with APP can be used to inhibit Aβ secretion in the brain, preventing and/or retarding the formation of amyloid plaque. In addition, agents suspected of having the desired activity can be screened for both effects on the interaction of APP with Fe65 (or other molecules containing PI domains) and effects on the Fe65 -dependent increase in secretion of Aβ. These agents or drugs are typically formulated in compositions for administration to mammalian patients in need of such therapy, and include those suffering from neurodegenerative disease where amyloid production is a causative agent such as Alzheimer's disease and dementia.

The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The therapeutic compositions are administered in a manner compatible with the dosage formulation, and in a therapeutically effective amount. The quantity to be administered depends on the subject to be treated, and the severity of the condition under treatment. Precise amount of active ingredient required to be administered depend on the judgment of the practitioner and are peculiar to each individual.

However, suitable dosages may range from about 0.1 to 20, preferably about 0.5 to about 10, and more preferably 1 to 5, milligrams of active ingredient per kilogram body weight of individual per day, and depend on the route of administration. Typically, the unit dosage form contains from about 0.5 mg to about 750 mg depending on the activity of the particular Fe65 modulator being utilized as the active ingredient.

EXAMPLES

The following examples are presented in order to more fully illustrate the preferred embodiments of the invention. They should in no way be construed, however, as limiting the broad scope of the invention.

Methods

Fe65 constructs

Fe65 was subcloned into the mammalian expression vector, pcDNA3 (Invitrogen) by PCR using Fe65 in pGEX (a gift of Tommaso Russo) as a template. The 5' PCR primer encoded an amino terminal FLAG epitope tag.

Stable Cell Lines

MDCK-695 cells were a generous gift of Christian Haas.[12] Cells were transfected in 10 cm diameter plates using the calcium phosphate transfection system (Gribco) essentially following the manufacturers instructions. Each plate was transfected with 15 μg of Fe65 in pcDNA3 and 5 μg of pPUR (Clontech), a selection vector containing a puromycin resistance gene. After selection with 2.5 μg/ml puromycin (Clontech), individual clones were isolated using cloning rings. Cell lines expressing high levels of Fe65 were identified by immunoblotting with polyclonal antibodies raised against a GST-fusion protein of amino acids 201–240 of Fe65. These cells are maintained in DMEM containing 200 μg/ml of G418 (Gibco) and 1 μg/ml of puromycin.

Immunoprecipitation

Immunoprecipitation was performed essentially as described previously.[13] Briefly, cells were plated at a density of 5×10⁴ cells/cm². After washing, they were incubated with [$^{35}S$]-methionine (NEN) in methionine-free Dulbeco's Modified Eagle Medium (DMEM, Gibco) for two hours at 37° C., followed by a two-hour chase at 37° C. in complete DMEM. APPs generated by α-cleavage and Aβ were immunoprecipitated from the chase medium with monoclonal antibodies 6E10 and 4G8 and agarose-linked goat anti-mouse IgG (American Qualex). Immunoprecipitates were separated by SDS-PAGE and quantified by PhosphorImager (Molecular Dynamics). Sister cultures were lysed with 1% NP40 in phosphate-buffered saline (PBS) immediately after labeling. Values obtained for APPs and Aβ were normalized to total labeled cellular holo/APP immunoprecipitated from these lysates with the polyclonal antibody raised against the cytoplasmic domain of APP.[14]

ELISA

For ELISAs, the cell medium was changed to fresh serum-free DMEM and incubated for four hours at 37° C. Then the conditioned medium was collected and subjected to sandwich ELISA for Aβ using 4G8 as the capture antibody and polyclonal antibodies FCA3340 or FCA3542 (from Frederic Checler) as the detection antibody. A more detailed description of the ELISA can be found elsewhere.[15] Samples were incubated with paramagnetic beads, biotinylated antibody and Origen TAG (IGEN) electrochemiluminescent-labeled antibody at 20° C. After 2 hours, Assay Buffer (IGEN) was added and AB was quantified using the IGEN Origen Analyzer. The values obtained were normalized to total cellular holoAPP determined by immunoblotting with 369 and [$^{125}$I]-protein A (Amersham) followed by PhosphorImager quantification.

While the invention has been described and illustrated herein by reference to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The documents should be considered as incorporated by reference in their entirety.

REFERENCES

1. Glenner, G. G. and Wong, C. W., *Biochemical & Biophysical Research Communications*, 120, 885–890 (1984).
2. Goldgaber, D.; Lerman, M. I.; McBride, O. W.; and Saffiotti, U. X., D. C., *Science*, 235, 877–880 (1987).
3. Kang, J.; Lamaire, H. G.; Unterbeck, A. et al., *Nature*, 325, 733–736 (1987).
4. Weidmann, A.; Konig, G.; Bunke, D.; Fischer, P.; Salbaum, J. M. X.; Masters, C. L.; and Beyreuther, K., *Cell* 57, 115–126 (1989).
5. Esch, F. S.; Keim, P. S.; Beattie, E. C. et al., *Science* 248, 1122–1124 (1990).
6. Seubert, P.; Vigo-Pelfrey, C.; Esch, F. et al, *Nature* 359, 325–327 (1992).
7. Haass, C.; Koo, E. H.; Mellon, A.; Hung, A. Y.; and Selkoe, D. J., *Nature* 357, 500–502 (1992).
8. Shoji, M.; Golde, T. E.; Ghisco, J. et al., *Science* 258, 126–129 (1992).
9. Duilio, A.; Zambrano, N.; Mogavero, A. R.; Ammendola, R.; Cimino, F.; and Russo, T., *Nucleic Acids Research* 19, 5269–5274 (1991).
10. Fiore, F.; Zambrano, N.; Minopoli, G.; Donini, V.; Duilio, A.; and Russo, T., *Journal of Biological Chemistry* 270, 30853–30856 (1995).
11. Zambrano, N.; Buxbaum, J. D.; Minopoli, G. X.; Fiore, F. et al., *Journal of Biological Chemistry* 272, 6399–6405 (1997).
12. Haass, C.; Koo, E. H.; Teplow, D. B.; and Selkoe, D. J., *Proceedings of the National Academy of Sciences of the United States of America* 91, 1564–1568 (1994).
13. Buxbaum, J. D.; Koo, E. H.; and Greengard, P., *Proceedings of the National Academy of Sciences of the United States of America* 90, 9195–9198 (1993).
14. Caporaso, G. L.; Gandy, S. L.; Buxbaum, J. D.; and Greengard, P., *PNAS* 89, 2252–2256 (1992).
15. Barelli, H.; Lebeau, A.; Vizza Vona, J. et al., *Molecular Medicine* (in press).

What is claimed is:

1. A method for screening for agents capable of modulating the interaction of Fe65 and the cytoplasmic domain of amyloid precursor protein (APP) which comprises:
    (a) providing a mammalian cell line which over-expresses both APP and Fe65 in culture;
    (b) optionally, radioactively labeling proteins produced by said cells during anabolism; then
    (c) allowing the mammalian cells to continue metabolizing in a suitable label-free environment;
    (d) contacting the mammalian cells at the start, or during step (c) with an agent suspected of being capable of modulating the interaction between Fe65 and the cytoplasmic domain of amyloid precursor protein;
    (e) lysing the mammalian cells;
    (f) measuring optionally labeled APPs and Aβ produced; and
    (g) comparing the measurements of step (f) with control cells not treated with the suspected agent.

2. The method according to claim 1 wherein the measurement of step (f) is by sandwich ELISA.

3. The method according to claim 1 wherein the measurement of step (f) is by immunoprecipitation.

4. The method according to claim 1 wherein the mammalian cell line is derived from Madin-Darby canine kidney (MDCK) cells.

* * * * *